US007001927B2

(12) United States Patent
Zhang et al.

(10) Patent No.: US 7,001,927 B2
(45) Date of Patent: *Feb. 21, 2006

(54) WATER REMOVAL IN FISCHER-TROPSCH PROCESSES

(75) Inventors: Jianping Zhang, Ponca City, OK (US); Harold A. Wright, Ponca City, OK (US); Yi Jiang, Ponca City, OK (US); Joe D. Allison, Ponca City, OK (US); Kenneth M. York, Ponca City, OK (US); Sergio R. Mohedas, Ponca City, OK (US); Vincent H. Melquist, Ponca City, OK (US)

(73) Assignee: ConocoPhillips Company, Houston, TX (US)

( * ) Notice: Subject to any disclaimer, the term of this patent is extended or adjusted under 35 U.S.C. 154(b) by 202 days.

This patent is subject to a terminal disclaimer.

(21) Appl. No.: 10/320,311

(22) Filed: Dec. 16, 2002

(65) Prior Publication Data

US 2003/0149121 A1   Aug. 7, 2003

Related U.S. Application Data

(63) Continuation-in-part of application No. 10/034,452, filed on Dec. 28, 2001, now Pat. No. 6,720,358.

(60) Provisional application No. 60/344,229, filed on Dec. 28, 2001, provisional application No. 60/344,228, filed on Dec. 28, 2001.

(51) Int. Cl.
| | |
|---|---|
| C07C 27/00 | (2006.01) |
| B01D 12/00 | (2006.01) |
| B01D 21/00 | (2006.01) |
| B01D 17/12 | (2006.01) |

(52) U.S. Cl. ............... 518/700; 518/705; 210/521; 210/523; 210/801; 210/805

(58) Field of Classification Search .......... 518/700, 518/705; 210/521, 523, 801, 805
See application file for complete search history.

(56) References Cited

U.S. PATENT DOCUMENTS

| | | | |
|---|---|---|---|
| 2,509,136 A | 5/1950 | Cornell | |
| 2,617,816 A | 11/1952 | Crowell et al. | |
| 3,432,036 A | 3/1969 | Kaiser | |
| 3,807,142 A | 4/1974 | Rich et al. | |
| 4,093,643 A | 6/1978 | Vannice et al. | |
| 4,428,839 A | 1/1984 | Davies et al. | |
| 4,520,215 A | 5/1985 | Owen et al. ............... 585/255 |
| 4,605,678 A | 8/1986 | Brennan et al. | |
| 4,973,453 A | 11/1990 | Agee | |
| 5,015,366 A | 5/1991 | Ruether et al. ............ 208/408 |
| 5,023,276 A | 6/1991 | Yarrington et al. | |
| 5,240,593 A | 8/1993 | Moredock | |
| 5,260,239 A | 11/1993 | Hsia | |
| 5,268,344 A | 12/1993 | Pedrick et al. | |
| 5,276,237 A | 1/1994 | Mieville | |
| 5,288,673 A | 2/1994 | Behrmann et al. | |
| 5,348,982 A | 9/1994 | Herbolzheimer et al. ... 518/700 |
| 5,407,644 A | 4/1995 | Rytter et al. ............... 422/147 |
| 5,422,375 A | 6/1995 | Rytter et al. ............... 518/700 |
| 5,520,890 A | 5/1996 | Lorentzen et al. ......... 422/197 |
| 5,527,473 A | 6/1996 | Ackerman | |
| 5,565,177 A | 10/1996 | Cetinkaya | |
| 5,639,798 A | 6/1997 | Wilson et al. ............. 518/714 |
| 5,770,629 A | 6/1998 | Degeroge et al. | |
| 5,811,469 A | 9/1998 | Leviness et al. | |
| 5,827,902 A | 10/1998 | Maretto et al. ............ 518/706 |
| 5,827,903 A | 10/1998 | White et al. | |
| 5,844,006 A | 12/1998 | Jager et al. | |
| 5,900,159 A | 5/1999 | Engel et al. | |
| 5,917,078 A | 6/1999 | Battosta et al. | |
| 5,939,350 A | 8/1999 | Singleton .................. 502/230 |
| 5,948,378 A | 9/1999 | Koveal et al. | |
| 5,958,985 A | 9/1999 | Geerling et al. | |
| 5,961,933 A | 10/1999 | Casanave et al. .......... 422/211 |
| 5,962,537 A | 10/1999 | Leviness | |
| 5,981,608 A | 11/1999 | Geerling et al. | |
| 6,060,524 A | 5/2000 | Casanave et al. .......... 518/706 |
| 6,068,760 A | 5/2000 | Benham et al. | |
| 6,069,179 A | 5/2000 | Rytter et al. | |
| 6,100,304 A | 8/2000 | Singleton et al. | |
| 6,114,400 A | 9/2000 | Nataraj et al. | |
| 6,156,809 A | 12/2000 | Clark et al. ............... 518/719 |
| 6,169,120 B1 | 1/2001 | Beer | |
| 6,191,066 B1 | 2/2001 | Singleton et al. | |
| 6,225,358 B1 | 5/2001 | Kennedy ................... 518/700 |
| 6,271,432 B1 | 8/2001 | Singleton et al. | |
| 6,277,338 B1 | 8/2001 | Agee | |
| 6,403,660 B1 | 6/2002 | Espinoza et al. .......... 518/700 |
| 6,462,097 B1 | 10/2002 | Martino et al. ............ 518/700 |

FOREIGN PATENT DOCUMENTS

FR        2807027        3/2000

(Continued)

OTHER PUBLICATIONS

PCT International Search Report for International Application No. PCT/US02/40239, dated Feb. 22, 2003 (6 p.).

(Continued)

Primary Examiner—J. Parsa
(74) Attorney, Agent, or Firm—Conley Rose P.C.

(57) ABSTRACT

A method for water removal in hydrocarbon product reactors operating at Fischer-Tropsch conditions. The water removal decreases the concentration of water in the reactor. In one embodiment, a method of reducing the concentration of water in a Fischer-Tropsch reactor containing a water-rich hydrocarbon product includes removing water from the water-rich hydrocarbon product of the reactor by a water removal means so as to form a water-reduced hydrocarbon product and returning that product to the reactor.

39 Claims, No Drawings

FOREIGN PATENT DOCUMENTS

WO 99/64380 12/1999

OTHER PUBLICATIONS

PCT International Search Report for International Application No. PCT/US02/40292 dated Feb. 23, 2003 (2 p.).

PCT International Search Report for International Application No. PCT/US03/21560, dated Nov. 17, 2003 (2 p.).

PCT International Search Report for International Application No. PCT/US02/41012 dated Mar. 9, 2003 (2 p.).

D. Schanke et al., *Study of the Deactivation Mechanism of $Al_2O_3$-Supported Cobalt Fischer-Tropsch Catalysts*, Catalysis Letters 34 (1995) pp. 269-284.

V.A. Kirillov et al., *A Mathematical Model of Fischer-Tropsch Synthesis in a Slurry Reactor*, Studies in Surface Science and Catalysis, vol. 119, A. Parmaliana et al. Ed., Elsevier Science, 1998, pp. 149-154.

Rothaemel, et al, "The effect of water on cobalt Fishcer-Tropsch catalysts studied by steady-state isotopic transient kinetic analysis (SSITKA)", Catalysis Today 38, 79-84, (1997).

D., Schanke, et al, "Reoxidation and Deactivation of Supported Cobalt Fischer-Tropsch Catalysts", Energy & Fuels, vol. 10, No. 4, 867-872, (1996).

A. M. Hilmen, et al, "Study of the effect of water on alumina supported cobalt Fishcer-Tropsch catalysts", Applied Catalysis A: General 186, 169-188, (1999).

Schulz et al., Applied Catalyst vol. 186 Nos. 1,2 Oct. 1999 (229 p.).

WATER REMOVAL IN FISCHER-TROPSCH PROCESSES

CROSS-REFERENCE TO RELATED APPLICATIONS

This application is related to commonly assigned, U.S. Utility application Ser. No. 10/034,452 now U.S. Pat. No. 6,720,358 entitled "Water Stripping and Catalyst/Liquid Product Separation System," co-pending Provisional Application Ser. No. 60/344,228 filed Dec. 28, 2001 and entitled "Method For Reducing Water concentration in a Multi-Phase Column Reactor," and co-pending Provisional Application Ser. No. 60/344,229 entitled "Water Removal in Fischer-Tropsch Processes" filed Dec. 28, 2001, each of which is hereby incorporated herein by reference.

STATEMENT REGARDING FEDERALLY SPONSORED RESEARCH OR DEVELOPMENT

Not applicable.

FIELD OF THE INVENTION

The present invention relates to a method for the preparation of hydrocarbons from synthesis gas, i.e., a mixture of carbon monoxide and hydrogen, typically labeled the Fischer-Tropsch process. Particularly, this invention relates to a method for water removal in Fischer-Tropsch reactors.

BACKGROUND OF THE INVENTION

Large quantities of methane, the main component of natural gas, are available in many areas of the world, and natural gas is predicted to outlast oil reserves by a significant margin. However, most natural gas is situated in areas that are geographically remote from population and industrial centers. The costs of compression, transportation, and storage make its use economically unattractive. To improve the economics of natural gas use, much research has focused on the use of methane as a starting material for the production of higher hydrocarbons and hydrocarbon liquids, which are more easily transported and thus more economical. The conversion of methane to hydrocarbons is typically carried out in two steps. In the first step, methane is converted into a mixture of carbon monoxide and hydrogen (i.e., synthesis gas or syngas). In a second step, the syngas is converted into useful hydrocarbons.

This second step, the preparation of hydrocarbons from synthesis gas, is well known in the art and is usually referred to as Fischer-Tropsch synthesis, the Fischer-Tropsch process, or Fischer-Tropsch reaction(s). Fischer-Tropsch synthesis generally entails contacting a stream of synthesis gas with a catalyst under temperature and pressure conditions that allow the synthesis gas to react and form hydrocarbons.

More specifically, the Fischer-Tropsch reaction is the catalytic hydrogenation of carbon monoxide to produce any of a variety of products ranging from methane to higher alkanes and aliphatic alcohols. Research continues on the development of more efficient Fischer-Tropsch catalyst systems and reaction systems that increase the selectivity for high-value hydrocarbons in the Fischer-Tropsch product stream.

There are continuing efforts to design reactors that are more effective at producing these desired products. Product distribution, product selectivity, and reactor productivity depend heavily on the type and structure of the catalyst and on the reactor type and operating conditions. Catalysts for use in such synthesis usually contain a catalytically active metal of Groups 8, 9, or 10 (in the New notation of the periodic table of the elements, which is followed throughout). In particular, iron, cobalt, nickel, and ruthenium have been abundantly used as the catalytically active metals. Cobalt and ruthenium have been found to be most suitable for catalyzing a process in which synthesis gas is converted primarily to hydrocarbons having five or more carbon atoms (i.e., where the $C_{5+}$ selectivity of the catalyst is high).

Originally, the Fischer-Tropsch synthesis was operated in packed bed reactors. These reactors have several drawbacks, such as difficulty of temperature control, which can be overcome by using gas-agitated slurry reactors or slurry bubble column reactors. Gas-agitated reactors, sometimes called "slurry reactors" or "slurry bubble columns," operate by suspending catalytic particles in liquid and feeding gas reactants into the bottom of the reactor through a gas distributor, which produces small gas bubbles. As the gas bubbles rise through the reactor, the reactants are absorbed into the liquid and diffuse to the catalyst where, depending on the catalyst system, they are converted to gaseous and/or liquid products. If gaseous products are formed, they enter the gas bubbles and are collected at the top of the reactor. Liquid products are recovered from the suspending liquid by passing the slurry through a filter that separates the liquid from the catalyst solids, and then separating the liquids.

A known problem in slurry reactors, however, is that water is continuously formed during Fisher-Tropsch synthesis in the reactors. This is known to limit conversion and prematurely deactivate catalyst systems such as iron and cobalt-based Fisher-Tropsch catalysts through an oxidation mechanism. As is well known in the art, a high water partial pressure correlates to a high deactivation rate. This is detrimental to the overall system performance, since two requirements for a successful commercial application of cobalt-based Fischer-Tropsch catalysts are a high conversion and, for middle distillates production, a high wax selectivity (or a high alpha value).

For any given cobalt-based catalyst, along with the $H_2/CO$ ratio and the reaction temperature, the total pressure is a parameter that has a direct influence on the wax selectivity, in that a higher pressure will result in a higher wax selectivity. However, a higher total pressure (at any given degree of conversion) also correlates to a higher water partial pressure and therefore a higher deactivation rate. Therefore, if reactors are operated at conditions conducive to higher alpha values, conversion will necessarily have to be low to avoid premature catalyst deactivation due to water. A low conversion is undesirable, however, because it results in higher capital investment and operating costs. Additionally, for iron-based catalysts, the water not only has a negative effect on the catalyst deactivation rate, but it also inhibits the rate of reaction.

The water partial pressure is therefore a constraint that will not allow the realization of the kinetic and/or wax selectivity potential of iron and cobalt-based Fisher-Tropsch catalysts. Therefore, in order to improve the efficiency of Fischer-Tropsch reactors using iron and cobalt-based catalyst systems, there exists a need for a method to remove water formed during Fisher-Tropsch synthesis.

SUMMARY OF THE INVENTION

The present invention relates to a method for water removal in reactors operating at Fischer-Tropsch conditions. More particularly, the present invention includes a water removal means capable of removing water dissolved in the wax, water contained in very small gas bubbles, and water adsorbed on the catalyst surface. This allows a higher conversion while protecting the catalyst from excessive oxidation. Further, by allowing a higher pass per conversion, fewer reactor stages may be necessary to achieve a suitable overall conversion.

In a preferred embodiment of the present invention, a method of reducing the concentration of water in a Fischer-Tropsch reactor containing a water-rich hydrocarbon product includes removing a portion of water from the water-rich hydrocarbon product means to form a water-reduced hydrocarbon product.

In a preferred embodiment of the present invention, a method of reducing the overall water concentration in a Fischer-Tropsch reactor comprises removing from the reactor a portion of the reactor content to generate a water-rich hydrocarbon stream; reducing the water concentration of the said water-rich hydrocarbon stream using a water removal means to create a water-reduced hydrocarbon stream; and returning at least a portion of the water-reduced hydrocarbon stream to the reactor.

In another preferred embodiment of the present invention, a method for producing hydrocarbons includes contacting a synthesis gas with a hydrocarbon synthesis catalyst in a Fischer-Tropsch reactor, under reaction conditions effective to form a product stream comprising hydrocarbons and secondary products, including water, from the synthesis gas. A portion of the product stream from the reactor then passes into a water removal zone and in which water is removed from the product stream to form water-reduced hydrocarbon product. Lastly, the water-reduced hydrocarbon product passes back into the reactor.

The present invention allows higher conversions of syngas and/or use of higher total pressures at any degree of conversion, while protecting the Fischer-Tropsch catalyst from an excessive oxidation rate. By returning the water-reduced hydrocarbon product back into the reactor, the water-reduced hydrocarbon product has time to undergo further reaction, forming a longer chain hydrocarbon product. Additionally, the water-reduced hydrocarbon product serves as a cooling agent that aids in controlling the reaction temperature by adding heat capacity and/or heat of vaporization to the system.

DETAILED DESCRIPTION OF THE PREFERRED EMBODIMENTS

According to the present invention, a water removal means may be employed to extract certain components, including water, from a Fischer-Tropsch process. In typical Fischer-Tropsch processes, water begins to accumulate in the operating reactor, forming a water-rich slurry that includes the hydrocarbon products. This is undesirable because water has a negative effect on the catalyst deactivation rate and tends to inhibit the rate of reaction. To minimize this problem, a portion of the water-rich slurry is passed through a water removal means to form a water-reduced hydrocarbon product. The water-reduced hydrocarbon product is then preferably exported or returned to the reactor. Thus, the concentration of water is reduced in the hydrocarbon product and in the Fischer-Tropsch reactor. Preferably at least 10% of overall water concentration is removed from the Fischer-Tropsch process, and more preferably at least 15% of overall water concentration is removed. Overall water concentration is herein defined as the amount of water per unit volume or mass of hydrocarbon product.

A number of different water removal means (i.e. separation methods) may be employed to remove water from the water-rich hydrocarbon product. Some of the means may be incorporated into the Fischer-Tropsch reactor itself, while others may be independent of the reactor and utilize a hydrocarbon product transport means. It is contemplated that in cases where the water removal means is independent of the reactor, gas-disengaging means may be utilized to ease separation. In addition, the different water removal means may be combined with each other in various arrangements to increase the efficiency of overall water removal. A few of the preferred separation methods are described below.

Separation by Phase Addition or Creation

One method of separation relies on the differences in solubility of a species in different phases of a substance. Thus, one method for causing a separation consists of creating or adding a second phase to a solution. Phase creation involves the creation of a second phase, which is immiscible with the feed phase. In the present invention, the feed phase is the water-rich hydrocarbon product. If the water-rich hydrocarbon product is a homogeneous single phase, then a second immiscible phase can be created by employing an energy-separating agent (ESA) or a mass-separating agent (MSA). One way to apply an ESA is to either change the temperature of the water-rich hydrocarbon product via heat transfer or shaft work such that a phase transition occurs. The equilibrium between the two immiscible phases having different compositions then results in separation. Similarly, by reducing the pressure in the system, a pressure-temperature and composition range can be attained such that two phases are in equilibrium, thus creating a second phase. On the other hand, adding material (an MSA) to the water-rich hydrocarbon product to cause a separation can also be used to cause creation of a second phase. The MSA may be partially immiscible with one or more of the species in the mixture. Alternatively, the MSA may be completely miscible with a liquid mixture to be separated, but may selectively alter the partitioning of species between liquid and vapor phases. When an MSA is used together with an ESA, a more complete separation can be achieved as in extractive distillation, for example.

If the separation by phase addition is applied with two liquid phases, immediate mixing of the liquids enhances the mass transfer rates between the liquids and separating agent and increases the rate at which the thermodynamic limit of partitioning of the components is attained. Once the two liquids are completely mixed and partitioning has occurred, the two liquids can be disengaged using mechanical means, for example gravity, or centrifugation.

Table 1 lists various separation methods based on phase creation or addition. These include partial condensation, flash vaporization, distillation, extractive distillation, reboiled absorption, stripping, azeotropic distillation, and liquid-liquid extraction.

TABLE 1

| Method | Feed Phase | New Phase | Agent |
|---|---|---|---|
| Partial Condensation | L/V | L/V | ESA |
| Flash Vaporization | L | V | P ↓ |
| Distillation | L/V | L/V | ESA |
| Extractive Distillation | L/V | L/V | ESA & MSA |
| Reboiled Absorption | L/V | L/V | ESA & MSA |
| Stripping | L | V | MSA |
| Azeotropic Distillation | L/V | L/V | MSA & ESA |
| Liquid-Liquid Extraction | L | L | MSA |

L = liquid, V = vapor, P ↓ = decrease in pressure

If the water-rich hydrocarbon product includes components that differ widely in their tendency to condense or vaporize, then partial vaporization or partial condensation might be appropriate. A vapor phase is partially condensed by removing heat, or less often by increasing pressure. Partial vaporization can be achieved by reducing pressure via flash vaporization. In either case, the partitioning of species occurs through interphase mass transfer such that the most volatile species are enriched in the vapor phase and the least volatile species concentrate in the condensed phase. The liquid and vapor phases are themselves usually disengaged by gravity.

When the liquids are miscible, separation may depend upon a difference in vapor pressure of the constituents. The utilization of this property is the basis of the operation known as distillation. If the volatility difference between the species to be separated is not large enough to cause the desired separation, then the separation process can be repeated on both the vapor and liquid phases. That is, the enriched vapor phase can be partially condensed, and the enriched liquid phase can be partially vaporized. The usual device for carrying out this chain of condensations and vaporizations is a distillation column. As vapor flows up the distillation column, it increases in concentration of the most volatile species, while the counterflowing liquid is enriched in the least volatile species. The initial hydrocarbon product is of concentration intermediate to vapor and liquid phases and is usually introduced at a tray near the midpoint of the column. The top part of the column is called the enriching or rectification section, while the lower section is called the stripping section. Rectification is herein defined as the purification of a liquid by redistillation. Liquid-vapor contact above the column is achieved using a condenser, while contact is provided in the stripping section via a reboiler to create reflux. The smaller the differences in volatility of the species, the greater the number of trays required in the distillation column. If the number of trays required for the desired separation is impractical, then a second column may be added or an MSA may be added to enhance separation. One combination of ESA and MSA that can be used is extractive distillation. The MSA is typically a solvent and enhances the volatility differences so as to reduce the number of trays needed in a column.

The MSA is usually the least volatile component in the mixture, completely miscible with the liquid phase and introduced near the top of the column. If the vapor at the top of the distillation column is not easily condensed by removing heat via heat transfer, then a liquid MSA absorbent may be used in place of reflux. This technique is called reboiled absorption, absorption refers to the process of a liquid absorbing a component from a vapor phase. The opposite case, where a vapor removes or strips a component of a liquid phase is known as stripping.

In one preferred embodiment of the present invention, the water removal means comprises stripping, wherein a stream of inert gas is introduced in countercurrent flow to the water-rich hydrocarbon product. In some embodiments, hydrogen is the preferred stripping gas. Introduction of the stripping gas to the hydrocarbon product reduces the water partial pressure in the reactor, creating a driving force for mass transfer from the liquid to the gas phase and forming a gaseous vapor phase comprising the stripping gas and water. The gaseous vapor phase may be condensed so that two phases are formed, namely a stripping agent rich phase and a water-rich phase. The stripping agent rich phase is preferably returned to the stripping process. Each phase may also contain trace amounts of other components, particularly the water-rich phase. It may be desirable to recover these trace amounts of ingredients such as oxygenated hydrocarbons from or entrained in the water-rich phase. Subsequent processing of the water-rich phase may be performed by processes known in the art to recover the material and render the water suitable for disposal. See co-pending U.S. Utility application Ser. No. 10/034,452 entitled "Water Stripping and Catalyst/Liquid Product Separation System," which is incorporated herein by reference.

The difference then between distillation and extractive distillation is that extractive distillation uses a MSA, while the difference between extractive distillation and reboiled absorption is that the condenser in reboiled absorption is replaced with an MSA feed. If the input mixture is a vapor and no stripping section is necessary, then the reboiled absorption is simply absorption. Conversely, if the feed is liquid, and no rectification section is needed, and the MSA is a stripper, then the operation is simply stripping. In another preferred embodiment of the present invention, the water removal means is absorption.

Another preferred technique that is useful in the present system is azeotropic distillation. Here, an MSA is added to the distillation column and forms a minimum boiling point azeotrope as an immiscible second phase. In addition to an MSA, several natural products from the Fischer-Tropsch reaction form natural azeotropes with water. These azeotropes then act as entrainers.

Unlike non-azeotropic mixtures, an azeotrope is a mixture of liquids that has a constant boiling point and thus cannot be separated by simple distillation. An azeotrope behaves as if it were a pure compound, and it distills from the beginning to the end of its distillation at a constant temperature, giving a distillate of constant azeotropic composition. The vapor in equilibrium with an azeotropic liquid has the same composition as the azeotrope. For example, light hydrocarbons (boiling point approximately 20° C. to 185° C.) and water (boiling point 100° C.) form a binary (two-component) azeotrope having a boiling point that is lower than either of the components and a composition that can be separated into the respective components on cooling. See Table 2 for examples of azeotropes contemplated in the present Fischer-Tropsch processes.

TABLE 2

| Azeotrope[a] | $BP_{atm}$, ° C. | $BPaz_{atm}$[b], ° C. | % Composition | | Hydrocarbon[c] $BP_{350psi}$, ° C. | $BPaz_{350psi}$, ° C.[d] |
| | | | Azeotrope | Upper Layer | Lower Layer | | |
| --- | --- | --- | --- | --- | --- | --- | --- |
| $C_5H_{12}$ | 36.1 | 34.6 | 98.6 | 99.95 | 0.04 | 175 | 168 |
| $H_2O$ | 100 | | 1.4 | 0.05 | 99.96 | | |
| $C_6H_{14}$ | 69 | 61.6 | 94.4 | | | 220 | 200 |
| $H_2O$ | 100 | | 5.6 | | | | |

TABLE 2-continued

| Azeotrope[a] | $BP_{atm}$, ° C. | $BPaz_{atm}$[b], ° C. | % Composition | | | Hydrocarbon[c] $BP_{350psi}$, ° C. | $BPaz_{350psi}$, ° C.[d] |
| --- | --- | --- | --- | --- | --- | --- | --- |
| | | | Azeotrope | Upper Layer | Lower Layer | | |
| $C_7H_{16}$ | 98.4 | 79.2 | 87.1 | 99.98 | 0.01 | 255 | 205 |
| $H_2O$ | 100 | | 12.9 | 0.02 | 99.99 | | |

[a]azeotropic data at atmospheric pressure from CRC Handbook of Chemistry and Physics, 54th edition, 1973;
[b]azeotrope boiling point at atmospheric pressure;
[c]hydrocarbon boiling points at 350 psi from FIG. A.1, API Recommended Practices 521, Guide for Pressure-Relieving and Depressuring Systems, p. 85;
[d]azeotrope boiling points at pressure extrapolated from atmospheric azeotropes according to $(BPaz_{atm}/BP_{atm}) \times (BP_{350psi})$.

Light hydrocarbons are herein defined as hydrocarbons having eight or less carbon atoms ($\leq C_8$). Because the boiling point of the azeotrope is lower that the boiling points of either of the two pure components, this is called a minimum boiling azeotrope. Fractional distillation or settling of the light hydrocarbon-water azeotrope is capable of producing a distillate that is greater than 95% hydrocarbons.

As mentioned above, one preferred water removal means is azeotropic distillation, wherein the water-rich hydrocarbon product comprises light hydrocarbons and water. Preferably the water-rich slurry is heated from approximately 150° C. to 250° C. to remove the binary azeotrope from the reactor. In some embodiments, the Fischer-Tropsch product may be allowed to distill from the reaction vessel at reaction temperature, carrying the water as the azeotrope with it, whereupon the azeotrope is condensed and separated via fractional distillation or settling as described above, yielding a water-rich phase and a hydrocarbon-rich phase. The water-rich phase is then removed. The distillate is preferably greater than 95% hydrocarbons, more preferably greater than 98% hydrocarbons. The water-reduced hydrocarbon-rich phase is preferably returned to the reactor. Condensation of this product in the condenser at 150° C. with an overall reactor pressure of 350 psia will allow for $C_{5+}$ hydrocarbons to be returned to the Fischer-Tropsch reactor.

Liquid-liquid extraction is a technique that is useful in cases where the mixture is temperature sensitive, and or when distillation is impractical. In this case a second liquid solvent is introduced to the hydrocarbon product. The second liquid selectively solvates a particular component or subset of components of the mixture. More than one solvent can be used at a time where additional solvents are sensitive to different components.

An important consideration in developing a successful separation method is selecting a good MSA. In general, selection criteria include the following:

i. Should enhance significantly the natural volatility of the key component.
ii. Should not require an excessive ratio of solvent to nonsolvent.
iii. Should remain soluble in the feed components and should not lead to the formation of two phases.
iv. Should be easily separable from the bottom product.
v. Should be inexpensive and readily available.
vi. Should be stable at the temperature of the distillation and solvent separation.
vii. Should be nonreactive with the components in the feed mixture.
viii. Should have a low latent heat.
ix. Should be noncorrosive and nontoxic.

Separation by Barrier

A technique that is used increasingly for industrial separations is barrier separations. Here a microporous or nonporous membrane is used as a semipermeable barrier for highly selective separations. Barriers can be solid (polymer, fiber, ceramic, metal, etc.) films, or less commonly liquid films in various geometric configurations. For microporous membranes separation occurs due to the difference in diffusivity through the pores of the membrane. For nonporous membranes the partitioning of species is due to both the differences of solubility in the membrane, and the rate of diffusion through the membrane. Membrane separation methods include osmosis, reverse osmosis, dialysis and microfiltration.

Osmosis occurs by diffusion down a concentration gradient through a membrane which is permeable to the solvent, but not to the solute. Solvent can then be moved across the membrane into the mixture until the concentrations on both sides of the membrane are equal. Reverse osmosis on the other hand requires that the solvent diffuse up the concentration gradient, which occurs when the feed pressure is above the osmotic pressure such that the solvent pressure gradient counterbalances the concentration gradient such that there is no driving force for solvent diffusion.

Separation by Solid Agent

Separation operations that use solid mass-separating agents often use a granular material, which acts as a support for a thin layer of absorbent or enters directly into the separation operation by selective adsorption or chemical reaction with certain species in the hydrocarbon product. Adsorption occurs only on the solid surface, whereas absorption occurs throughout the bulk of the liquid absorbent. The solid agent must be replaced or refreshed periodically since saturation occurs with time. This necessitates the need for batchwise or semicontinuous modes of operation. Regeneration or refresh of the solid adsorbents can occur through desorption of the adsorbate. In this case, the ability to separate depends on the selective adsorption of the components.

Separation by External Field or Gradient

The above separation techniques rely on the differences in chemical potential of a component in two phases to effect a separation. In addition to the chemical interactions that produce differences in solubility, vapor pressure, etc. external fields can also be employed to partition components that respond differently to the imposed field. Centrifugation and settling can separate components by weight as the heaviest particles have larger centrifugal forces on them. Large temperature gradients can be used to create thermal diffusion where different species diffuse at different rates along thermally induced concentration gradients. Electrolysis is another field separation technique. In this case, the field causes differing rates in chemical reaction in an electrochemical cell. Electrophoresis exploits the different transport velocities of charged colloidal, or suspended particles in an electric field.

As discussed above, the means for separating one liquid from another depends on whether or not the two liquids are miscible. If they are not, and do not form an emulsion, it is necessary only to provide an opportunity for the two to separate into layers according to their specific gravities. These two layers may be drawn off from different levels. This procedure is known as decantation, or settling, and allows the lower specific gravity layer lying above the higher specific gravity layer, to be poured very gently away from the higher specific gravity layer, which remains in the original vessel.

In still another preferred embodiment of the present invention, the water removal means is decantation. Decantation may be performed within a Fischer-Tropsch reactor, or may be performed in a separate vessel. Because solubility increases with temperature, by decreasing the temperature in the vessel, the water forms a separate phase or layer from the hydrocarbons. In a preferred embodiment, the temperature in the vessel is decreased to approximately 65° C. to 125° C. In the case of a two-phase vessel where light hydrocarbons and water form separate phases, the light hydrocarbon phase generally has a lower specific gravity than the water phase and therefore floats. The water phase may be removed by draining the vessel from the bottom (also called intermittent separation) until the hydrocarbon phase begins to drain.

In intermittent separation, a discharge pipe set in a swivel joint inside the vessel is convenient. The end of this pipe either may be attached to a float, which ensures that the inlet end of the pipe is always just a little below the surface of the lower specific gravity layer, or may be lowered by a chain. Alternatively, a flexible tube attached to the exit portion of the pipe may be employed.

In the case of a three-phase system in which light hydrocarbons, water, and heavy hydrocarbons form three separate phases, the light hydrocarbon phase generally has a lower specific gravity than the water phase, and the water phase generally has a lower specific gravity than the heavy hydrocarbon phase. Therefore, the heavy hydrocarbon phase is at the bottom of the vessel, the light hydrocarbon phase is at the top of the vessel, and the water phase is in between the two hydrocarbon phases. Heavy hydrocarbons are herein defined as hydrocarbons having nineteen or more carbons ($C_{19+}$). In three phase vessels, a boot shape or "boot" may be desirable so that two drains may coexist and that the heavy hydrocarbons may be collected as product while the water may be removed from the vessel.

As discussed above, if the two liquids are so nearly the same density that they do not easily separate, it is sometimes expedient to add a substance soluble in one in order that it may acquire a specific gravity materially greater than the other.

If the force of gravity alone is not sufficient to separate two liquids, as is the case in many emulsions, of if separation by gravity is tool slow, centrifugal force may be employed. When the mixture is fed into a vessel that is rotating at a high rate of speed, the heavier liquid is thrown to the outside of the vessel, while the lighter liquid remains in the center of the vessel. The two vertical layers will rise to the top of the rotating vessel as the operation continues, and, by suspending a diaphragm in to the dividing lines, the two layers may be drawn off from separate exit spouts.

In another preferred embodiment of the present invention, the water separation means is centrifugation. Preferably, a hydrocyclone is used to exert a centrifugal force on the water-rich hydrocarbon product. The hydrocyclone may be a forward, reverse, or a through-flow cleaner. Forward cleaners are traditional hydrocyclones, where high specific gravity contaminants are released from the bottom tip of the cyclone while desired products are collected from the top. The reverse and through-flow cleaners are for removing lower specific gravity contaminants. In a preferred embodiment, the hydrocyclone is a forward cleaner.

Fischer-Tropsch Operating Conditions

The feed gases charged to the process of the preferred embodiment of the present invention comprise hydrogen, or a hydrogen source, and carbon monoxide. $H_2$/CO mixtures suitable as a feedstock for conversion to hydrocarbons according to the process of this invention can be obtained from light hydrocarbons such as methane by means of steam reforming, partial oxidation, or other processes known in the art. Preferably the hydrogen is provided by free hydrogen, although some Fischer-Tropsch catalysts have sufficient water gas shift activity to convert some water to hydrogen for use in the Fischer-Tropsch process. It is preferred that the molar ratio of hydrogen to carbon monoxide in the feed be greater than 0.5:1 (e.g., from about 0.67 to 2.5). Preferably, the feed gas stream contains hydrogen and carbon monoxide in a molar ratio of about 2:1. The feed gas may also contain carbon dioxide. The feed gas stream should contain a low concentration of compounds or elements that have a deleterious effect on the catalyst, such as poisons. For example, the feed gas may need to be pre-treated to ensure that it contains low concentrations of sulfur or nitrogen compounds such as hydrogen sulfide, ammonia and carbonyl sulfides.

The feed gas is contacted with a catalyst in a reaction zone. Mechanical arrangements of conventional design may be employed as the reaction zone including, for example, fixed bed, fluidized bed, slurry phase, slurry bubble column, reactive distillation column, or ebullating bed reactors, among others, may be used. Accordingly, the size and physical form of the catalyst particles may vary depending on the reactor in which they are to be used.

The Fischer-Tropsch process is typically run in a continuous mode. In this mode, typically, the gas hourly space velocity through the reaction zone may range from about 50 $hr^{-1}$ to about 10,000 $hr^{-1}$, preferably from about 300 $hr^{-1}$ to about 2,000 $hr^{-1}$. The gas hourly space velocity is defined as the volume of reactants per time per reaction zone volume. The volume of reactant gases is at standard conditions of pressure (1 atm or 101 kPa) and temperature (0° C. or 273.16 K). The reaction zone volume is defined by the portion of the reaction vessel volume where reaction takes place and which is occupied by a gaseous phase comprising reactants, products and/or inerts; a liquid phase comprising liquid/wax products and/or other liquids; and a solid phase comprising catalyst. The reaction zone temperature is typically in the range from about 160° C. to about 300° C. Preferably, the reaction zone is operated at conversion promoting conditions at temperatures from about 190° C. to about 260° C. The reaction zone pressure is typically in the range of about 80 psia (552 kPa) to about 1000 psia (6895 kPa), more preferably from 80 psia (552 kPa) to about 600 psia (4137 kPa), and still more preferably, from about 140 psia (965 kPa) to about 500 psia (3447 kPa).

The products resulting from the process will have a great range of molecular weights. Typically, the carbon number range of the product hydrocarbons will start at methane and continue to the limits observable by modern analysis, about 50 to 100 carbons per molecule. The process is particularly useful for making hydrocarbons having five or more carbon atoms especially when the above-referenced preferred space velocity, temperature and pressure ranges are employed.

The wide range of hydrocarbons produced in the reaction zone will typically afford liquid phase products at the reaction zone operating conditions. Therefore the effluent stream of the reaction zone will often be a mixed phase stream including liquid and vapor phase products. The effluent stream of the reaction zone may be cooled to effect the condensation of additional amounts of hydrocarbons and passed into a vapor-liquid separation zone separating the liquid and vapor phase products. The vapor phase material may be passed into a second stage of cooling for recovery of additional hydrocarbons. The liquid phase material from the initial vapor-liquid separation zone together with any liquid from a subsequent separation zone may be fed into a fractionation column. Typically, a stripping column is employed first to remove light hydrocarbons such as propane and butane. The remaining hydrocarbons may be passed into a fractionation column where they are separated by boiling point range into products such as naphtha, kerosene and fuel oils. Hydrocarbons recovered from the reaction zone and having a boiling point above that of the desired products may be passed into conventional processing equipment such as a hydrocracking zone in order to reduce their molecular weight. The gas phase recovered from the reactor zone effluent stream after hydrocarbon recovery may be partially recycled if it contains a sufficient quantity of hydrogen and/or carbon monoxide.

While the present invention has been disclosed and described in terms of a preferred embodiment, the invention is not limited to the preferred embodiment. For example, while the present invention has been described for use in a slurry bubble column reactor, it should be understood that any Fischer-Tropsch reactor, including but not limited to fixed bed reactors, fluidized bed reactors, catalytic distillation reactors, trickle bed reactors, and continuously stirred tank reactors (CSTR) may be used. In addition, various modification to the operating conditions and stripping gases, among others, can be made without departing from the scope of the invention. In the claims that follow, any sequential recitation of steps is not intended as a requirement that the steps be performed sequentially, or that one step be completed before another step is begun, unless explicitly so stated.

What is claimed is:

1. A method of reducing the overall water concentration in a Fischer-Tropsch reactor comprising:
   a) removing from the reactor a portion of the reactor content to produce a water-rich hydrocarbon stream;
   b) reducing the water concentration of the water-rich hydrocarbon stream to create a water-reduced hydrocarbon stream; and
   c) returning at least a portion of the water-reduced hydrocarbon stream to the reactor.

2. The method according to claim 1 wherein at least 10% of overall water concentration is removed from the Fischer-Tropsch reactor.

3. The method according to claim 2 wherein at least 15% of overall water concentration is removed from the Fischer-Tropsch reactor.

4. The method according to claim 1, further including degassing the water-rich hydrocarbon stream prior to step b).

5. The method according to claim 1 wherein step b) includes using a phase addition or phase creation separation technique.

6. The method according to claim 5 wherein step b) includes partial condensation.

7. The method according to claim 6 wherein an energy-separating agent (ESA) is employed.

8. The method according to claim 5 wherein step b) includes flash vaporization.

9. The method according to claim 8 wherein pressure in the reactor is decreased during step b).

10. The method according to claim 5 wherein step b) includes distillation.

11. The method according to claim 10 wherein an energy-separating agent (ESA) is employed.

12. The method according to claim 5 wherein step b) includes extractive distillation.

13. The method according to claim 12 wherein an energy-separating agent (ESA) and a mass-separating agent (MSA) are employed.

14. The method according to claim 5 wherein step b) includes azeotropic distillation.

15. The method according to claim 14 wherein an azeotrope exists between water and light hydrocarbons in the water-rich hydrocarbon stream.

16. The method according to claim 15 wherein step b) includes heating the water-rich hydrocarbon stream from approximately 150° C. to 250° C. to remove the azeotrope from the reactor.

17. The method according to claim 16, further including condensing the azeotrope into a distillate comprising a water-rich phase and a hydrocarbon-rich phase.

18. The method according to claim 17 wherein the phases are separated by fractional distillation or settling.

19. The method according to claim 17 wherein the water-rich phase is removed from the distillate.

20. The method according to claim 19 wherein the distillate comprises at least 95% light hydrocarbons.

21. The method according to claim 20 wherein the distillate comprises at least 98% light hydrocarbons.

22. The method according to claim 15 wherein an energy-separating agent (ESA) and a mass-separating agent (MSA) are employed.

23. The method according to claim 5 wherein step b) includes absorption.

24. The method according to claim 23 wherein step b) includes reboiled absorption.

25. The method according to claim 24 wherein an energy-separating agent (ESA) and a mass-separating agent (MSA) are employed.

26. The method according to claim 5 wherein step b) includes stripping.

27. The method according to claim 26 wherein an inert, stripping gas is introduced counter-current to the water-rich hydrocarbon stream.

28. The method according to claim 27 wherein the stripping gas is essentially hydrogen.

29. The method according to claim 5 wherein step b) includes liquid-liquid extraction.

30. The method according to claim 29 wherein a mass-separating agent (MSA) is employed.

31. The method according to claim 1 wherein step b) includes a barrier separation.

32. The method according to claim 1 wherein step b) includes separation using a solid agent.

33. The method according to claim 1 wherein step b) includes the application of an external field or gradient.

34. The method according to claim 33 wherein step b) includes decantation.

35. The method according to claim 34 wherein step b) includes decreasing the temperature in the reactor to approximately 65° C. to 125° C. to form a water phase and a light hydrocarbon phase.

36. The method according to claim 35 wherein intermittent separation removes the water phase from the reactor.

37. The method according to claim 33 wherein step b) includes centrifugation.

38. A method for producing hydrocarbons comprising:
a) contacting a synthesis gas with a hydrocarbon synthesis catalyst in a Fischer-Tropsch reactor, under reaction conditions effective to form a product stream comprising hydrocarbons and secondary products, including water, from the synthesis gas;
b) passing a portion of the product stream from the reactor into a water removal zone and removing water from the product stream to form water-reduced hydrocarbon product; and
c) passing at least a portion of the water-reduced hydrocarbon product back into the reactor.

39. The method according to claim 1 wherein the portion of the reactor content removed in step a) comprises a slurry.

* * * * *

UNITED STATES PATENT AND TRADEMARK OFFICE
CERTIFICATE OF CORRECTION

PATENT NO.    : 7,001,927 B2
DATED         : February 21, 2006
INVENTOR(S)   : Jianping Zhang et al.

It is certified that error appears in the above-identified patent and that said Letters Patent is hereby corrected as shown below:

<u>Title page,</u>
Item [75], Inventors, add -- Rafael L. Espinoza, Ponca City, OK (US) --.

Signed and Sealed this

Second Day of May, 2006

JON W. DUDAS
*Director of the United States Patent and Trademark Office*